United States Patent [19]

White

[11] Patent Number: 5,984,995
[45] Date of Patent: Nov. 16, 1999

[54] HEAT CELLS

[75] Inventor: Richard Keim White, Maineville, Ohio

[73] Assignee: The Procter & Gamble Company, Cincinnati, Ohio

[21] Appl. No.: 08/623,752

[22] Filed: Mar. 29, 1996

[51] Int. Cl.[6] .................................................. C22C 33/00
[52] U.S. Cl. ........................... 75/230; 75/246; 252/67; 126/263.05; 607/114; 44/250; 419/65; 419/66
[58] Field of Search ........................... 75/230, 243, 246, 75/252, 253; 607/114; 126/263.05; 44/250; 252/67; 419/65, 66

[56] References Cited

U.S. PATENT DOCUMENTS

| Re. 32,026 | 11/1985 | Yamashita et al. | 126/263 |
| 3,976,049 | 8/1976 | Yamashita et al. | 126/263 |
| 3,980,070 | 9/1976 | Krupa | 126/263 |
| 4,093,424 | 6/1978 | Yoshida et al. | 44/3 C |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,649,895 | 3/1987 | Yasuki et al. | 126/263 |
| 4,925,743 | 5/1990 | Ikeda et al. | 428/702 |
| 5,046,479 | 9/1991 | Usui | 126/204 |
| 5,233,981 | 8/1993 | Miyashita | 607/114 |
| 5,342,412 | 8/1994 | Ueki | 607/114 |
| 5,366,492 | 11/1994 | Ueki | 607/114 |

FOREIGN PATENT DOCUMENTS

| 1086110 | 5/1994 | China | A43B 7/02 |
| 0045642 | 2/1982 | European Pat. Off. | A61F 7/03 |
| 160433 | 7/1987 | India | C09K 3/02 |
| 56-145846 | 11/1981 | Japan | A61F 7/03 |
| 56-170252 | 10/1982 | Japan | A61F 7/03 |
| 58-37075 | 3/1983 | Japan | C09K 5/00 |
| 58-132074 | 8/1983 | Japan | C09K 5/00 |
| 3-100090 | 4/1991 | Japan | C09K 5/00 |
| 4-2342 | 1/1992 | Japan | A61F 7/08 |
| 4-293989 | 10/1992 | Japan | C09K 5/00 |
| 5-81261 | 11/1993 | Japan | A61F 7/08 |
| 5-317188 | 12/1993 | Japan | A47J 36/28 |
| 6-1969 | 1/1994 | Japan | C09K 5/00 |
| 6-241575 | 8/1994 | Japan | F24J 1/02 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-194641 | 8/1995 | Japan | A61F 7/08 |
| 7-194642 | 8/1995 | Japan | A61F 7/08 |
| 2205496 | 12/1988 | United Kingdom | A61F 7/03 |
| 2 301 433 | 12/1996 | United Kingdom | F24J 1/00 |

OTHER PUBLICATIONS

"Oral Solid Dosage Forms", Remington's Pharmaceutical Scienses, 18th edition, 1990, Alfonso R. Gennaro, ed., pp. 1633–1656.

U.S. application No. 08/604,694, Burkett et al., filed Feb. 21, 1996.

*Primary Examiner*—Ngolan Mai
*Attorney, Agent, or Firm*—Loy M. White; Douglas C. Mohl; T. David Reed

[57] ABSTRACT

This invention relates to a method of manufacturing heat cells which are based on a specific iron oxidation chemistry and having specific physical dimensions and fill characteristics. This method uses direct compaction of powdered ingredients into granules, pellets, tablets, slugs, and/or the like. These heat cells, which can be incorporated into disposable body wraps, provide a controlled and sustained temperature for consistent, convenient, and comfortable heat application for treating temporary or chronic pain. This invention also relates to said exothemic compositions incorporated into said heat cells.

21 Claims, No Drawings

HEAT CELLS

TECHNICAL FIELD

This invention relates to a method of manufacturing heat cells which incorporate exothermic compositions comprising dry-compacted heating elements such as granules, pellets, tablets, slugs, and the like. These heat cells can be easily incorporated into disposable body wraps and the like, which adapt to a wide variety of body contours, providing consistent, convenient, and comfortable heat application to the wearer. This invention also relates to said exothemic compositions incorporated into said heat cells.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like. These treatments include the use of whirlpools, hot towels, hydrocollators, heating pads and elastic compression bands. Many of these devices employ reusable thermal packs containing, e.g., water and microwaveable gels. In general, such devices which require the thermal source to be replenished are inconvenient to use. Further, many of these thermal units or devices do not provide long lasting heat and also do not maintain a consistent temperature over long periods of time. The skin temperature needs to be maintained from about 38° C. to about 41° C. but not above 45° C., as tissue damage occurs above 45° C., to achieve the desired therapeutic benefits.

The beneficial therapeutic effects from this administration of heat diminishes after the heat source is removed; therefore, it is desirable to provide a sustained heat source to the afflicted area for as long as possible, preferably for about eight hours. Disposable heat packs based on iron oxidation, such as those described in U.S. Pat. Nos. 4,366,804, 4,649,895, 5,046,479, and Re. 32,026 are known and can provide long-lasting heat. However, such devices have proven not totally satisfactory. Many of these devices cannot maintain a consistent and controlled temperature and/or such thermal devices are bulky and have unsatisfactory physical dimensions which hinder their effectiveness. Specifically, such devices cannot be easily incorporated into wraps which can comfortably conform to various body contours and hence deliver inconsistent, inconvenient and/or uncomfortable heat application to the body.

A major reason these heating devices can not maintain a consistent and controlled temperature is due to the considerable empty space within the pack after the pack is filled with the heat generating composition, which inevitably causes uneven distribution or agglomeration of the composition in the pack, especially since these devices generally stand substantially perpendicular or at a slight slant when the heat pack is applied to the body. Uneven distribution of the heat generating composition makes the heat generation in the pack uneven and the agglomeration results in an unpleasant feel to the pack for the user. The agglomeration of the composition also causes uneven heat generation because it disturbs the supply of oxygen to the iron particles which is needed for the oxidation reaction to occur. In order for these heating devices to generate a uniform heat, the heat generating composition must be placed in the pack in a flat form, such as the heat packs of Usui in U.S. Pat. No. 5,046,479. The heat packs of Usui have an air permeability, which allows oxygen to enter the bag while creating a reduction in the pressure within the bag as the oxidation reaction occurs, thereby holding the composition in place and maintaining the bags flat form while applied to the body. This, however, requires very careful selection of both, the components for the particulate composition and the material for the heat pack bag. Specifically, this method allows very little variation in the air permeability of the bag material, which can occur between different manufactured lots of the air permeable material. This method also does nothing to solve the problems associated with controlling the carbon dust or the uniformity of the composition during filling of the heat pack and/or the finished heat pack during use.

In Japanese Kokai Patent Application No. HEI 06-315498, Kodama discloses that, while heat packs having a low packing density have good oxygen permeability and are able to reach their maximum temperature quickly, the temperature decreases rapidly. This is primarily due to the uneven distribution of the heat generating composition within the pack. On the other hand, Kodama discloses that the heat generating composition cannot be packed too densely. If the packing density is high, the heat pack never reaches its highest temperature or maximum duration. This is due to the inability of oxygen to penetrate the heat generating composition beyond its surface, which results in the incomplete reaction of the entire composition, i.e., the center of the composition remains unreacted.

There are several major problems in the manufacture of disposable heat packs, utilizing the exothermic reaction of iron oxidation, wherein the ingredients are blended dry. For example, one major problem is the carbon powder tends to become airborne easily and therefore a problem, in that raw materials are lost and the working environment is hazardous, both for the health and safety of persons working in the manufacturing area of such heat packs. Special facilities must be maintained, as well as, special clothing and equipment must be worn by the manufacturing workers. A second major problem, related to the dry powdered carbon, occurs during the manufacture of the finished heat pack. That is, the powdered carbon tends to fly out of or overflow the intended fill space of the heat pack during the filling process such that the heat pack margins become soiled with carbon dust preventing effective sealing of the powdered exothermic composition inside the finished heat pack. A third problem is maintaining the uniformity of the dry powdered ingredients in the particulate exothermic composition after blending. That is, once uniformly blended, the composition, which contains particles of different weights and densities, may shift or settle during the manufacturing process such that the finished heat pack may not contain a uniform mixture of the composition, thereby reducing the performance of the heat pack. A fourth problem is the lack of fluidity of the dry powder mixture during the manufacturing process, largely due to the electrostatic adherence of the powdered particles to the containers and/or equipment.

One method of reducing these problems is disclosed by Hatsumoto in Japanese Kokai Patent Application No. HEI 06-241575, in which Hatsumoto adds a small percentage of the total water to the carbon before blending it with the other dry ingredients. While this method reduces the amount of carbon dust, it requires that the amount of water added to the carbon, prior to blending, be carefully and precisely measured, and the preferred embodiment requires that the wetted carbon stand for at least 24 hours before blending with the other ingredients. This method, still does not guarantee the uniform content of the particulate exothermic composition or address the other manufacturing problems mentioned above.

Another method of reducing these problems is disclosed by Watabe in Japanese Kokoku Patent No. HEI 05-081261.

Watabe utilizes magnetic transfer of pre-wetted powdered ingredients, in the shape and thickness of the desired heat pack, to a sheet of material used for the pack. The remaining water is then sprayed onto the powdered ingredients immediately prior to a second sheet being placed on top of the magnetic sheet containing the wetted ingredients. The sheets are then sealed, enclosing the wetted ingredients to form the desired heat pack. The pack is cut out of the bonded sheets and quickly placed into an oxygen-impermeable protective package. This method is more efficient and less labor intensive than the method of Hatsumoto, but it still can not guarantee the uniform content of the particulate exothermic composition, and requires very specialized machinery.

In another method of reducing these problems Odama discloses, in Japanese Kokai Patent Application No. HEI 04-293989, using a wet granulation method wherein an adhesive binder, such as polyvinyl alcohol, carboxymethyl cellulose, hydroxypropyl cellulose, and polyvinylpyrrolidone, is added to water and dissolved, before the water is added to the other ingredients. When the water-binder solution is added to the other ingredients, pellets are formed. These wetted pellets are then packed into gas-permeable bags. This method requires a large amount of water, 55–70parts, by weight of the composition, and binder, 10–20 parts, by weight of the composition, to be added to the exothermic mixture. This reduces the carbon dust and increases the fluidity of the mix, as well as improves the uniformity of the mixture content, but requires careful maintenance of the water added to the composition, as well as an inert atmosphere during the manufacturing process.

The inventor of the present invention has developed dry-compacted heating elements comprising a specific iron oxidation chemistry for incorporation into heat cells having specific physical dimensions and fill characteristics, as well as methods of manufacturing said heating elements and heat cells. These heat cells can be easily incorporated into disposable body wraps and the like, which adapt to a wide variety of body contours, thus providing consistent, convenient, and comfortable heat application. The present invention uses dry agglomeration and/or a direct compaction technique, usually used in the tablet and slugging operations of pharmaceuticals, to overcome the aforementioned problems associated with the current heat packs and their manufacture. Content uniformity of the particulate exothermic composition is maintained through electrostatic and pendular agglomeration, i.e., the enhancement of normal electrostatic forces, by pre-treating the powder blend with low levels of liquefied polysaccharide(s) or modifiers prior to compaction. Once agglomerated, the ingredients are formed as slugs or tablets of a pre-measured, dust-free composition which requires only the on-line addition of water or brine for activation.

Agglomeration of the high surface area powder blend with the low levels of agglomeration aids, such as polysaccharide(s) or modifiers, required in the present invention is unexpected, i.e., the ratio of powder surface area to agglomeration aid is very large and therefore, the use of much higher levels of agglomeration aids should be required. The low levels of agglomeration aids allows for a more efficient use of dry binders, added to the exothermic compositions to aid in the binding together of carbon and iron, and produces a hard compaction without excessive dilution of the reactants.

Alternatively, direct compaction using a roller compactor and chelsenator, a tablet press slugging operation and chelsenator, or roller compactor modified to produce pellets, can be used to produce small granules/pellets, which are useful for a controlled, dust-free packing operation of the heat cells of large size or irregularly shaped configurations. The present invention, which is substantially free of water in the compaction process, reduces the carbon dust, eliminates various manufacturing problems, increases the line speed and fill weight accuracy, improves fluidity of the exothermic composition, eliminates the non-uniformity of the exothermic composition within the finished heat cell, improves the performance of the finished heat cell, and eliminates the need for specialized equipment and environments, all of which significantly reduces the labor required, health and safety hazards, and overall cost of manufacturing.

The heat cells, incorporating heating elements manufactured according to the methods of the present invention and based on a specific iron oxidation chemistry, have specific physical dimensions and fill characteristics, providing long lasting heat generation with improved temperature control. The heat cells contain a dry-compacted particulate heat generating material which substantially fills the available cell volume within the cell reducing any excess void volume thereby minimizing the ability of the heat generating material to shift within the cell. This is accomplished without the need for any differential pressure across the cell wall. These heat cells, because of their adaptable physical dimensions, can be easily incorporated into disposable body wraps and the like which adapt to a wide variety of body contours, thus providing consistent, convenient, and comfortable heat application.

It is therefore an object of the present invention to provide dry, compacted particulate heating elements, and methods of manufacturing said elements, using direct compaction of powdered ingredients, comprising carbonaceous material and iron, capable of reaching their maximum temperature quickly and providing a controlled and sustained temperature, for incorporation into exothermic heat cells. These heat cells are then easily incorporated into disposable body wraps which adapt to a wide variety of body contours providing consistent, convenient and comfortable heat application.

These objectives and additional objectives will become readily apparent from the detailed description which follows.

SUMMARY OF THE INVENTION

A method of manufacturing exothermic heat cells comprising mixing a particulate exothermic composition comprising from about 30% to about 80% of iron powder, from about 3% to about 20% of dry powdered carbonaceous material, from about 0% to about 9% of an agglomeration aid, and from about 0% to about 35% of a dry binder to be formed as dry agglomerated granules, direct compaction articles, and/or mixtures thereof. Additionally, from about 0.5% to about 10% of a metal salt, is added to the dry mix or subsequently as an aqueous solution. Preferably the dry agglomerated granules, direct compaction articles, and/or mixtures thereof are packed into a pocket having a top and bottom cell-forming surface, which when sealed forms a unified structure, such as a heat cell, comprising at least two opposed surfaces, wherein at least one surface is oxygen permeable. An aqueous solution is added to the dry agglomerated granules, direct compaction articles, and/or mixtures thereof before or after sealing said surfaces to form said unified structure. The dry agglomerated granules, direct compaction articles, and/or mixtures thereof have a density of greater than 1 $g/cm^3$. The direct compaction articles preferably comprise granules, pellets, tablets, and/or slugs, wherein said tablets and/or slugs comprise a geometric shape selected from the group consisting of a disk, triangle, square, cube, rectangle, cylinder, and ellipsoid, as well as specific physical dimensions. Similarly, the finished heat cells comprise a shape selected from the group consisting of a disk, triangle, pyramid, cone, sphere, square, cube, rectangle, rectangular parallelepiped, cylinder, and ellipsoid having specific physical dimensions and fill characteristics.

All percentages and ratios used herein are by weight of the total composition, and all measurements made at 25° C., unless otherwise specified.

DETAILED DESCRIPTION OF THE INVENTION

The present invention provides a method of manufacturing exothermic heat cells, using direct compaction of powdered ingredients, comprising carbonaceous material and iron, to form heating elements, capable of providing a controlled and sustained temperature, reaching their maximum temperature quickly, and being easily incorporated into disposable body wraps which adapt to a wide variety of body contours providing consistent, convenient and comfortable heat application.

"Heat cells", as used herein, means a unified structure, comprising an exothermic composition having a specific iron oxidation chemistry enclosed within top and bottom sheets, wherein at least one sheet is oxygen permeable, capable of providing long lasting heat generation with improved temperature control, and having specific physical dimensions and fill characteristics. These heat cells can be used as individual heating units, or because of their adaptable physical dimensions, can be easily incorporated into disposable body wraps and the like which adapt to a wide variety of body contours, thus providing consistent, convenient, and comfortable heat application.

"Agglomerated pre-compaction composition", as used herein, means the mixture of dry powdered ingredients, comprising iron powder, carbonaceous powder, metal salt(s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/ solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

Iron Powder

The heat cells manufactured according to the methods of the present invention, generate heat by the exothermic oxidation of iron. In order for this electrochemical reaction to occur several elements must be present, i.e., an anode, a cathode, water, and oxygen. Within the specific iron oxidation chemistry of the heat cells described herein, iron serves as the anode for the reaction. Suitable sources for iron powder include, but not limited to, cast iron powder, reduced iron powder, electrolytic iron powder, scrap iron powder, pig iron, wrought iron, various steels, iron alloys, and the like, as well as treated varieties of these iron powders. There is no particular limitation to their purity, kind, etc., so long as it can be used to produce heat-generation with electrically conducting water and air. However, the preferred iron powders have large reactive surface areas and small particle size.

Typically, the iron powder comprises from about 30% to about 80%, preferably from about 40% to about 70%, most preferably from about 50% to about 65% by weight, of the agglomerated pre-compaction compositions of the present invention.

Carbonaceous Materials

Although most any carbonaceous materials may be used, activated carbon is particularly useful in the heat cells of the present invention, in that it serves a multiple purpose. Its primary purpose is to serve as the cathode for the electrochemical reaction involved in the exothermic oxidation of iron and its secondary purpose is as a water-holding material. Active carbon is extremely porous in the inner structure giving it particularly good oxygen- and water-retention capabilities. Moreover, active carbon not only absorbs water well as mentioned above, but also adsorbs water vapor evaporated by the heat generation of the exothermic composition and helps prevent the escape of the water vapor. Further, active carbon can adsorb odors such as those caused by the oxidation of iron powder.

Active carbon prepared from coconut shell, wood, charcoal, coal, bone coal, etc. are useful, but those prepared from other raw materials such as animal products, natural gas, fats, oils and resins are also useful in the heat cells of the present invention. There is no limitation to the kinds of active carbon used, however, the preferred active carbon has superior water holding capabilities and small particle size. While activated carbon is the preferred carbon, non-activated types prepared from coconut shell, wood, coal, and the like, are also useful for the compositions and methods described herein. The cathode capabilities may also be extended by using non-activated, soft, carbon powder, i.e., carbon blended to reduce cost. Therefore, mixtures of the above carbons are useful in the methods and compositions of the present invention as well.

Carbonaceous materials, typically activated carbon, non-activated carbon, and mixtures thereof, comprise from about 3% to about 20%, preferably from about 5% to about 15%, most preferably from about 6% to about 12% by weight, of the agglomerated pre-compaction compositions of the present invention.

Metal Salts

The metal salt serves as a reaction promoter (electrolyte) by activating the surface of the iron to facilitate the oxidation reaction and provides electrical conduction between the anode (iron) and cathode (activated carbon) of the exothermic composition to sustain the corrosive reaction. The metal salt is typically added as a dry powder to the particulate exothermic composition of the present invention before agglomeration, but may also be added to the exothermic compositions in the water as a salt (brine) solution. Metal salts which are useful in the present invention are the alkali, alkaline earth, and transitional metal salts which includes sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Other suitable alkali, alkaline earth, and transition metal salts also exist which can be used, alone or in combination, to sustain the corrosive reaction of iron. Also, carbonate salts, acetate salts, nitrates, nitrites and other salts can be used.

Among these metal salts, the deliquescent salts such as calcium chloride, magnesium chloride, etc., are very hygroscopic and hence these compounds, even when added in a small amount, show an effectiveness in inhibiting the escape of water vapor. Sodium chloride shows only a small solubility difference vs. temperature difference and hence, no crystal is precipitated at low temperatures, and also provides reasonable heat-generation. Thus, deviation of heat-generation due to temperature difference of atmospheric air does not occur. Because of this, as well as its low cost and suitability, sodium chloride is the preferred metal salt of the exothermic composition of the present invention.

Typically, the metal salt(s) comprises from about 0.5% to about 10%, preferably from about 1% to about 8%, most preferably from about 2% to about 6% by weight, of the agglomerated pre-compaction compositions of the present invention.

Agglomeration Aids

Maintaining the content uniformity of powders after mixing and prior to compaction is a primary concern. While some uniformity occurs naturally from the free surface energy and electrostatic forces found with the small particles of the compositions described herein, it is not particularly reliable or robust when these mixtures are handled during the manufacturing process. The present invention solves this problem by agglomerating the essential reaction chemistry using low levels of agglomeration aids prior to the addition of dry binders necessary for a hard compaction. These agglomeration aids, which are essentially concentrated syrups containing from about 70% to about 85% solids and from about 15% to about 30% bound water or pure polyols containing from about 1% to about 5% water, are used in low levels, not normally expected to form agglomeration granules or "micro-granules". The free water levels of the pre-compaction composition are low enough, i.e., less than about 3%, preferably less than 2%, that the exothermic chemical reaction does not occur while mixing. Traditionally, granulation has been achieved using dilute solutions, where water is essential and wet massing occurs, with or without binders. The agglomeration methods of the present invention are accomplished not by wet massing the particulate but by enhancing the strength of the electrostatic forces already present. The results of this enhancement is a somewhat pendular agglomeration, which appears slightly wet yet is not, wherein all parts of the mix are uniformly distributed, defined granules are found, and dust is eliminated from the mix. As a secondary benefit, this agglomeration essentially reduces the total surface area of the particulate in the mixture which allows for lower levels of dry binder to yield a hard compaction. Agglomeration also allows for the uniform mixing of particles with a large size variance, extending the availability of carbon and iron blends which normally separate after mixing. The agglomerate may also be used as the final exothermic composition of the present invention when compaction is not desired. Examples of agglomeration aids which are useful, but not limited to, in the present invention include gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup.

The preferred agglomerating aids for the present invention, based primarily on cost and usefulness capability are crystallizing sorbitol, amorphous sorbitol, corn syrup, maltitol syrup, and mixtures thereof.

Typically, agglomeration aids comprise from about 0% to about 9%, preferably from about 0.5% to about 8%, more preferably from about 0.6% to about 6%, most preferably from about 0.7% to about 3% by weight, of the agglomerated pre-compaction compositions of the present invention.

The amount of free water present in the pre-compaction composition when the most preferred level of agglomeration aids are used in the present invention is less than about 1%.

Dry Binders

Since iron and carbon do not compact easily, binders which are capable of binding fine powder under dry conditions and at low concentration while producing a non-friable granulation, must be added to the exothermic particulate compositions. Dry binders which are useful, but not limited to, in the present invention include maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate. The preferred dry binding agent of the present invention is microcrystalline cellulose.

While the amount of dry binder added to the compositions of the present invention depend on the degree of hardness desired, dry binders typically comprise from about 0% to about 35%, preferably from about 4% to about 30%, more preferably from about 7% to about 20%, most preferably from about 9% to about 15% by weight, of the agglomerated pre-compaction compositions of the present invention.

Aqueous Solution

The aqueous solution typically used in the present invention is water. However, water may also serve as a solvent for dissolving and carrier for delivering the metal salt and added to the exothermic compositions of the present invention in the form of a brine solution. The water used herein may be from any appropriate source. There is no particular limitation to its purity, kind, etc.

The amount of aqueous solution added to the exothermic compositions of the present invention depends on the type and amount of iron to be added, the aqueous solution typically, comprises from about 10% to about 50%, by weight of the compaction articles, preferably from about 15% to about 40%, by weight of the compaction articles, most preferably from about 15% to about 30%, by weight of the compaction articles of the present invention.

Additional Components

In addition to the components of the exothermic compositions of the present invention described above, other components may also be added as appropriate.

While oxygen is necessary for the oxidation reaction of iron to occur, an internal oxygen source is not required in the heat cells of the present invention, however, oxygen-producing chemical materials may be incorporated in the particulate exothermic composition at the time of preparation thereof without changing the scope of the present invention. The oxygen sources used for the purpose of this invention include air and artificially made oxygen of various purity. Among these oxygen sources, air is preferred since it is the most convenient and without expense.

Although active carbon has superior water holding capabilities and can fulfill the requirement of a water-holding material in the present invention, additional water-holding materials absorb the aqueous solution of the reaction promoter beyond the limits of active carbon and serves the function of gradually supplying the promoter and water to the coexistent iron powder without wetting the iron surfaces.

Additional water-holding materials which are useful in the present invention include vermiculite, zeolite, porous silicates, wood powder, wood flour, cotton cloth having a large amount of fluffs, short fibers of cotton, paper scrap, vegetable matter, carboxymethylcellulose salts, and other porous materials having large capillary functions and hydrophilic properties.

The reaction chemistry of the present invention can be extended, i.e., the more complete oxidation of all the iron, by the addition of excess water. The containment of this water is achieved by the addition of super absorbents alone or in combination with the additional water-holding materials listed above. That is, super absorbent water-swellable or water-soluble polymers and resins and methacrylic acid resins and derivatives thereof, may be used as additional water-holding materials in the present invention, especially when used in combination with less absorbent materials such as those listed above. These resins may be prepared by the polymerization of a water-soluble monomer or a monomer that can acquire water solubility by means of hydrolysis, having double bonds that can undergo additional polymerization with starch and/or cellulose, followed by cross-linking and, if needed, hydrolysis, to form the desired resin. Examples of the aforementioned monomers include acrylic acid, methacrylic acid, maleic anhydride, and other monomers containing carboxyl groups, sodium salts of acrylic acid and methacrylic acid, trimethacrylic salt, triethanolamine salt, and other monomers containing carboxylic acid bases. Typical examples of the polymers/resins useful in the present invention include the acrylic acid salt starch co-polymer such as SanWet IM1000, available from Hoechst Celeanese, and isobutylene maleic anhydride co-polymer such as Isoban, available from the Kuraray Company of Japan. These highly water-absorptive polymers and polymer resins are commonly used in sanitary products and diapers and may also be used as additional water-holding materials in the present invention.

The preferred additional water-holding materials in the present invention include vermiculite, carboxymethylcellulose and salts thereof, acrylic acid salt starch co-polymer, isobutylene maleic anhydride co-polymer, and mixtures thereof.

While the type and amount of additional water-holding materials added to the exothermic compositions of the present invention depends on the amount of water to be added, if used, additional water-holding materials typically comprise from about 0.5% to about 10%, preferably from about 0.5% to about 6%, most preferably from about 0.5% to about 4% by weight, of the agglomerated pre-compaction compositions of the present invention.

Disintegrants may also be included in the exothermic compositions of the present invention to help open the structure of the compaction articles to allow oxygen access to the compressed reaction components. Disintegrants useful in the compositions of the present invention include starches, modified starches such as sodium glycollate starch, microcrystalline cellulose, water-soluble cellulose derivatives such as carboxymethyl cellulose, sodium alginate, alginic acid, clays, cross-linked polyvinylpyrrolidone, ion exchange resins, and modified cellulose gum such as croscarmellose sodium, and mixtures thereof.

Other disintegrants which may be used in the present invention include alkyl metal carbonate, such as sodium bicarbonate, in combination with a soluble acid, such as citric acid, malic acid, and acid salts such as sodium dihydrogen phosphate.

The preferred disintegrants of the present invention are microcrystalline cellulose, croscarmellose sodium, and mixtures thereof.

If used, disintegrants typically comprise from about 0.1% to about 6%, preferably from about 0.5% to about 5%, most preferably from about 1% to about 3% by weight, of the agglomerated pre-compaction compositions of the present invention.

Lubricants and flow agents may be added to the exothermic compositions of the present invention to improve the flow rate of the exothermic composition, to limit the wear on dies and punches, reduce inter-particle friction, and help facilitate the ejection of the tablets from the die cavity. Lubricants and flow agents useful in the compositions of the present invention include micronized salt, microfine vermiculite, stearic acid, metallic stearates, hydrogenated vegetable oils, partially hydrogenated vegetable oils, animal fats, corn starches, talc, microfine silicas, polyethylene glycol, light mineral oil, sodium benzoate, micronized polyethylene spheres, and mixtures thereof. The preferred lubricant of the present invention is magnesium stearate, while the preferred flow agent of the present invention is micronized salt, microfine vermiculite, microfine silica, and mixtures thereof.

Iron powder usually undergoes the oxidation reaction and generates heat when exothermic compositions are prepared according to the present invention. However, certain types of iron are known, which do not undergo oxidation or undergo only a slow oxidative reaction. The addition of oxidation reaction enhancers, such as elemental chromium, magnesium, or copper, compounds comprising said elements, or mixtures thereof, to the non-/slow-reactive iron powder makes it more oxidizable. Therefore, oxidation reaction enhancers may be added to the exothermic compositions of the present invention.

Inorganic or organic alkali compounds or alkali weak acid salts such as sodium hydroxide, potassium hydroxide, sodium hydrogen carbonate, sodium carbonate, calcium hydroxide, calcium carbonate, and sodium propionate may be incorporated in the particulate exothermic composition of the present invention to prevent the generation of gas, i.e., hydrogen gas, during the oxidation reaction of the iron powder, especially untreated iron powder or iron in the presence of acid salts. Iron treated with sulfates/sulfides may also be used in the present invention to inhibit the formation of hydrogen gas.

Fillers function as a heat buffer to inhibit a sudden change in temperature due to heat generation and radiation and also as a heat preserver to retain heat. The fillers may be porous, permeable to air, and have a low specific gravity. Fillers which may be useful in the particulate exothermic composition of the present invention include natural fibers in staple form such as wood dust, cotton linter and cellulose, synthetic fibers in staple form such as polyester staple fibers, waste of foamed synthetic resins such as foamed polystyrene and polyurethane, and other materials such as silica powder, porous silica-gels, sodium sulfate, barium sulfate, iron oxides, aluminum oxides, vermiculite, and mixtures thereof.

Anti-caking agents may also be useful in the particulate exothermic compositions of the present invention. Anti-caking agents which may be useful include tricalcium phosphate and sodium silicoaluminate.

Other additional components include thickeners, such as cornstarch, potato starch, carboxymethylcellulose, and α-starch, and surfactants such as those included within the anionic, cationic, nonionic, zwitterionic, and amphoteric types. The preferred surfactant is, but not limited to, non-ionic. Still other additional components which may be added to the exothermic compositions of the present invention, as appropriate, include extending agents such as metasilicates, zirconium, and ceramics.

Particle Size Range

Preferably at least 50%, more preferably 70%, even more preferably 80% and most preferably 90% of all of the dry powder particles by weight of the exothermic compositions of the present invention have a mean particle size of less than 200 μm, preferably less than 100 μm.

Method of Manufacturing Heat Cells

Heat cells, manufactured according to the methods of the present invention, incorporate heating elements, have specific physical dimensions and fill characteristics, and provide long lasting heat generation with improved temperature control. The heat cells contain a dry agglomerated, and/or direct compacted particulate heat generating material, based on a specific iron oxidation chemistry, which substantially fills the available cell volume within the cell reducing any excess void volume, thereby minimizing the ability of the heat generating material to shift within the cell. These heat cells, because of their adaptable physical dimensions, can be easily incorporated into disposable body wraps and the like which adapt to a wide variety of body contours, thus providing consistent, convenient, and comfortable heat application.

Heat cells of the present invention may be made by incorporating dry agglomerated granules of the agglomerated pre-compaction composition into the heat cell pocket. That is, the dry powdered components of the present invention, except water, are blended, using conventional blending techniques and agglomerated into granules. Suitable methods of blending these components are described in detail in U.S. Pat. No. 4,649,895 to Yasuki et al., issued Mar. 17, 1987 which is incorporated by reference herein. For example, powdered carbon and a metal salt are added to a blender or mixer, and blended into a uniform dry mixture. An additional water-holding material is added and the composition is mixed until uniform. For this particular method of making heat cells, dry binders may be optionally added to the composition along with the additional water-holding material. Powdered iron is added and the mixture is again blended until uniform. An agglomeration aid is then added to the blended powders. The composition is mixed until a light agglomeration is formed and no dust appears. The granules may be placed directly into a heat cell pocket, direct compacted into compaction articles, and/or stored in low humidity for later use. The agglomerated granules useful in the exothermic compositions of the present invention are easily wetted, less dense particles and soft porous granules which may be sufficient in some applications. The granules formed by the agglomeration process may be optionally "rounded" on a rotary granulator, and fines reattached prior to being placed into a heat cell pocket.

Heat cells of the present invention are preferably made by direct compaction of the dry ingredients into compaction articles such as hard granules, pellets, tablets, and/or slugs. For example, powdered carbon and a metal salt are added to a blender or mixer, and blended into a uniform dry mixture. Powdered iron and a disintegrant are added to the carbon/salt mixture and blended until the new mixture is uniform. An agglomeration aid is added to the blended powders. The composition is mixed until a light agglomeration is formed and no dust appears. An additional water-holding material is then added to the agglomeration. Gentle mixing continues until the additional water-holding material is evenly dispersed in the agglomeration. A dry binder is added to the agglomeration and the composition is mixed until uniform. The mixture is then transferred to a rotary tablet press and compressed into disk shaped tablets having a hole passing perpendicular through the middle of the top and bottom surfaces, having concaved top and bottom surfaces, i.e., double whisper design, or other shapes forming a reservoir conducive to holding water. These compacted tablets can be stored in low humidity for later use or placed into pockets formed in a unified structure comprising at least two opposed surfaces, i.e., top and bottom sheets, wherein at least one surface is oxygen permeable. In the later case, a pocket is formed in a sheet of cell-forming material and the tablet is placed into the pocket. A second sheet of cell-forming material is placed over the first sheet of cell-forming material, such that the tablet is between the two sheets of material. The two sheets are sealed around the edges of the pocket containing the tablet. The sealed pocket is then cut out of the cell-forming material sheets to form the finished heat cell or incorporated into, for example, body wraps such as knee, neck, back, etc. These heat cells or wraps can be stored in low humidity for later use.

In a variation of the method described above, the pre-compaction composition may be compressed into a slug, having no particular shape, or a tablet which lacks the hole or reservoir, rather, the tablet comprises any standard tablet configuration including spherical, convexed shallow face, convexed standard face, convexed deep face, flat face, and capsule, flat edge, beveled edge, oval, and modified ball. Therefore, after the tablet is placed into the pocket in the cell-forming material sheet, water or brine is added to the tablet, dropwise, immediately prior to the second cell-forming material sheet being placed over the first cell-forming material sheet. The wetted tablet is sealed between the two cell-forming material sheets and placed into an oxygen impermeable secondary package, which may be optionally evacuated of oxygen and sealed. The heat cells may be stored for later use or incorporated into, for example, body wraps as above.

Suitable methods of making tablets and/or slugs are described in detail in Chapter 89, "Oral Solid Dosage Forms", *Remington's Pharmaceutical Sciences,* 18th Edition, (1990), pp. 1634–1656, Alfonso R. Gennaro, ed., incorporated herein by reference in its entirety. Any conventional tableting machine and compression pressures, up to the maximum provided by the machine can be used in the methods of the present invention.

It is also possible to form compaction articles such as granules, tablets, and/or slugs which can be incorporated into the heat cells by first compacting the pre-compaction composition into a ribbon and then granulating the ribbon. For example, blending of the dry powdered iron, carbon, salt, and disintegrant, agglomerating with an agglomeration aid, adding an additional water-holding material, and dry binder is performed as described above. However, for this process the pre-compaction mixture is transferred to a roller compactor and compressed into a ribbon. The ribbon is passed through an oscillating granulator or grinder. The resulting granules may be used "as is" or a screen may be set up to collect only the granules having a preferred size of from about 250 μm to about 850 μm. The fines which are not collected by the screen, may be recycled through the compaction process or may be reattached to the outside of the granules, using a rotary granulator, with an agglomeration aid such as polysaccharide syrup to form sphere-shaped particles. This process provides more rapid heat generation, i.e., start-up, from the exothermic composition due to the more reactive dust surface on the particle. The granules can be placed directly into a pocket as described above, re-compacted into tablets/slugs, or stored in low humidity for later use.

Small pellets may also be made from the pre-compaction composition using, for example, a modified roller compactor. In this method the pre-compaction composition may be compressed in a roller compactor equipped with embossed rollers to produce small pellets of from about 3 mm to about 4 mm in diameter which may then be placed directly into a pocket as described above, compacted into tablets/slugs, or stored in low humidity for later use. Pellets made according to this method provide the advantages of uniform shape and surfaces and eliminates dust, as well as the need for an oscillating granulator or grinder.

Advantages of a densely compacted exothermic composition include extended heat generation, the exothermic composition is easily wetable, and the hard compacted form is suitable for separate manufacture and distribution. Also there is no dust from the compaction articles, unlike the fine powdered components of the exothermic composition, when said composition is added to the heat cell pockets, and compaction articles provide a premeasured dose size of the exothermic composition added to the heat cell pocket which eliminates on-line weight checks of the heat cell prior to the addition of water, as well as reduces the composition and performance variability between individual heat cells.

Activation of the cells is accomplished by injecting water or salt solution, i.e., by needle, through the oxygen permeable cell-forming material sheet into the hole or reservoir in the middle of the tablet, or into the granular composition. Since the heat cell will begin to generate heat shortly after activation if exposed to air, the heat cell, or wherein the heat cell is incorporated into a body wrap, the wrap, is placed immediately into an oxygen impermeable secondary package, which may be optionally evacuated of oxygen, and then sealed.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet. The hole or reservoir serves multiple purposes. For example, it allows rapid adsorption of the water into the particulate exothermic composition to speed start-up and provide an even reaction throughout the compaction article, reduces or eliminates the center of the tablet which is least likely to oxidize during the iron oxidation reaction, and reduces the weight and concentrates the chemistry within a specific area to maximize the strength of the tablet of the finished heat cell.

While the compaction articles of the present invention have significant advantages over the powdered compositions of the previously disclosed heat packs, the different tablet configurations also have advantages over each other. For example, tablets comprising a hole provide increased line speed over the double whisper tablet configuration which is faster than the line speed for flat-faced slugs.

A water-carrying material having hydrous property and flexibility such as superabsorbents, a spongy body, paper, synthetic resin-foam, rubber, cellulose, and the like may be placed in the hole or reservoir to gradually supply the water to the compressed particulate composition to prolong the exothermic reaction.

The size of the disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 0.7 cm, preferably from about 0.15 cm to about 0.6 cm, more preferably from about 0.2 cm to about 0.55 cm, and most preferably from about 0.2 cm to about 0.5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are typically compressed to a density of greater than about 1 $g/cm^3$, preferably from about 1 $g/cm^3$ to about 3 $g/cm^3$, more preferably from about 1.5 $g/cm^3$ to about 3 $g/cm^3$, and most preferably from about 2 $g/cm^3$ to about 3 $g/cm^3$.

The compaction articles of the present invention are also compressed to the hardest possible mechanical strength. For example, tablets require a certain amount of mechanical strength (i.e. hardness) to withstand the shocks of handling in their manufacture, packing, shipping, and dispensing. Although hardness is not a fundamental property, diametral crushing is most frequently used for in-process control because of its simplicity.

Tablet hardness is defined as the force required to break a tablet in a diametral compression test. This test consists of placing the tablet between two anvils and applying pressure to the anvils until the tablet breaks. The crushing strength that just causes the tablet to break is recorded. Hardness is thus sometimes referred to as "tablet crushing strength."

Several instruments have been developed for measuring tablet hardness in this manner. These include the Stokes (Monsanto) tester, the Strong-Cobb tester, the Pfizer tester, the Erweka tester, the Heberlein (or Schleuniger) tester, the Key tester, and the Van der Kamp tester. The hardness of a tablet is a function of many things all working together. Hardness is a function of applied compressional force and is therefore a function of those factors that cause the force to vary. For example, variation in tablet thickness may produce variations in tablet hardness. As additional force is applied to compress a tablet, the tablet hardness will increase. This relationship will hold up to a maximum value beyond which increases in pressure will not cause an increase in hardness, but will cause the tablet to laminate or cap, thus destroying its integrity.

The methods of the present invention produce hard and non-laminating tablets. Hardness is determined using a Erweka hardness tester as described above. Typically, a 2 gram, 1.9 cm diameter, double whisper tablet, prepared under 10 tons of pressure, can be made to withstand 400 newtons force, depending on the specific tablet formulation, i.e., tablets which contain maltitol syrup as the agglomeration aid yield the highest force numbers and are therefore the hardest tablets.

When filled with a compaction article such as granules, pellets, tablets, or slugs, and water added to form a heating element, the pocket has a fill volume, void volume, and a cell volume. The compressed tablets, slugs, pellets, and/or granules swell axially from about 50% to about 80% of their compacted size, depending on the specific chemistry of the compaction article, after water is added to them, conforming to the heat cell pocket constraints. The fill volume, as used herein, means the volume of the compacted, water-swelled, heating element in the finished heat cell. The void volume, as used herein, means the volume of the cell left unfilled by the compacted, water-swelled, heating element in a finished heat cell, not including the unfilled space within a tablet comprising a hole or reservoir, measured without differential pressure in the heat cell and without additional stretching or deformation of the cell-forming material. The cell volume, as used herein, means the fill volume plus the void volume of the heat cell. The ratio of fill volume to cell volume is from about 0.7 to about 1.0, preferably from about 0.75 to about 1.0, more preferably from about 0.8 to about 1.0, even more preferably from about 0.85 to about 1.0, and most preferably from about 0.9 to about 1.0.

The finished heat cell can have any geometric shape, e.g., disk, triangle, pyramid, cone, sphere, square, cube, rectangle, rectangular parallelepiped, cylinder, ellipsoid and the like. The preferred shape of the heat cells manufactured according to the present invention, comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells manufactured according to the present invention have a height of from about 0.15 cm to about 1 cm, preferably from about 0.3 cm to about 0.9 cm, more preferably from about 0.4 cm to about 0.8 cm, and most preferably from about 0.4 cm to about 0.7 cm resulting in a cell volume of from about 0.0047 $cm^3$ to about 79 $cm^3$, preferably from about 0.05 $cm^3$ to about 46 $cm^3$, more preferably from about 0.3 $cm^3$ to about 16 $cm^3$, and most preferably from about 0.7 $cm^3$ to about 5 $cm^3$. Alternatively, the heat cells having geometric shapes other than a disk shape may have a width at its widest point of from about 0.15 cm to about 5 cm, preferably from about 0.3 cm to about 1 cm, a height at its highest point of from about 0.15 cm to about 5 cm, preferably from about 0.3 cm to about 1 cm, and a length of from about 1 cm to about 20 cm, preferably from about 5 cm to about 10 cm, resulting in a cell volume of from about 0.015 $cm^3$ to about 500 $cm^3$, preferably from about 0.35 $cm^3$ to about 10 $cm^3$.

The heat cells manufactured according to the present invention preferably have a total surface area of below about 50 $cm^2$, preferably below about 40 $cm^2$, even more preferably below about 25 $cm^2$, and more preferably below about 20 $cm^2$.

The preferred heat cells of the present invention typically comprise, as described above, a pre-formed pocket in a bottom surface of cell forming material, wherein the exothermic composition is placed into the pocket and covered by a top surface of cell forming material. The exothermic composition is sealed between the two surfaces. However, heat cells of the present invention may also comprise being placed into a pocket formed by sealing two surfaces of cell forming material, wherein at least one surface is air-permeable, on all sides except leaving one side unsealed. The exothermic composition may be inserted into the pocket by way of the unsealed side. The heat cells may be flattened under a roller, such that the air inside the pocket is expelled, and sealed or sealed allowing the air inside the pocket to freely traverse the air-permeable surface. The heat cells made by this method will retain composition uniformity and original shape, even when applied vertically to the body. These heat cells may be stored for later use or incorporated into, for example, body wraps as above.

Cell-forming Material

The cell-forming material can be made of any suitable materials. However, the preferred material for the cell-forming sheets of the present invention is a film capable of forming a pocket using mechanical means, heat, and/or vacuum. Examples of such films are polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber and synthetic rubber.

The cell-forming sheets of the present invention may also be film layer substrates made of nonwoven fabric, to provide support, laminated to a film having heat sealability and capable of being easily thermally fused. A liquefied silicone rubber coating may also be applied to the non-woven fabric. For the non-woven fabrics, those having preferred characteristic properties of light weight and high tensile strength, e.g., nylon, rayon, cellulose ester, polyvinyl derivatives, polyolefins, polyamides, or polyesters, cuproammonium cellulose (Bemberg) and other high molecular weight compounds, as well as natural materials such as, wool, silk, jute, hemp, cotton, linen, sisal, or ramie, are suitable. These nonwoven materials are generally described in Riedel "Nonwoven Bonding Methods and Materials", *Nonwoven World*, (1987), incorporated herein by reference in its entirety. Examples of the film are polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber and synthetic rubber. The film layer substrates thickness is in the range of about 1 to about 300 $\mu$m and may be oxygen permeable or impermeable. The preferred film layer substrates of the present invention are polypropylene nonwoven sheets laminated to a film of poly(ethylene-vinyl acetate) or low-density polyethylene (LDPE) and having a thickness of about 5 to about 100 $\mu$m.

Web material composed of continuous filaments of thermoplastic resin laminated with a thermoplastic resin film, such as those described in Japanese Kokai Patent Application No. HEI 07-067907, published Mar. 14, 1995, incorporated herein by reference in its entirety, may also be useful in the present invention.

The opposed surfaces can be created by bonding two cell-forming sheets together around their periphery thereby forming a pouch, envelope, or pocket. In the case wherein film layer substrates are used, the film side in placed toward the inside of the pouch, envelope, or pocket (the side to be filled) and the nonwoven side to the outside. Pockets can also be made in the cell-forming sheets by thermoforming, mechanical embossing, vacuum embossing, or other acceptable means. Thermoforming is described in "Thermoforming", *The Wiley Encyclopedia of Packaging Technology*, pp. 668–675 (1986), Marilyn Bakker, ed., incorporated herein by reference in its entirety.

Individual heat cells can typically be prepared by adding a tablet, comprising a hole in the middle, of the exothermic composition to the preformed pocket in a sheet of low-density polyethylene film. A flat sheet of poly(ethylene-vinyl acetate) film is placed over the pocket containing the tablet. The two film sheets are bonded together using a low heat, forming a unified structure. The resulting heat cell contains the tablet sealed in the pocket between the two film sheets. Water is then injected, i.e., by needle, through the oxygen-permeable film sheet into the hole in the center of the tablet.

Alternatively, it is possible to form the pocket around the compaction articles using vacuum and heat. For example, the bottom sheet of film is heated and vacuum is used to draw the film into a mold. The compaction articles are placed into the vacuum formed pockets. The compaction articles are then activated with water, a top sheet of film is placed over the bottom sheet containing the pockets, and the two sheets are sealed enclosing the compaction articles between the top and bottom sheets as described above for slugs, or the heat cell is sealed and then activated with water, as described above for tablets. After the two cell-forming sheets are bonded together, the vacuum is released allowing the heated film to contract around the compaction articles.

It is also possible, and preferred in the present invention, to form the pocket(s) using vacuum without heat.

Heat cells may also be prepared by using magnet force, alone or with vacuum, exerted by magnets in the bottom of the mold, to hold the compaction articles comprising the magnetic iron in place within the vacuum formed or preformed pockets in the bottom cell-forming sheet. A second cell-forming sheet is then placed over the first cell-forming sheet, such that the compaction articles are between the two sheets. The compaction articles are then sealed between the top and bottom cell-forming sheets. Another alternative uses magnetic transfer of a fixed amount of the granulated exothermic composition to the pocket in the LDPE film sheet. That is, magnetic force is used to hold the granulated composition in place on the cell-forming sheet. A second cell-forming sheet is then placed over the first cell-forming sheet, such that the granulated composition is between the two sheets. The granulated composition is then sealed between the top and bottom cell-forming sheets.

Oxygen permeability can be provided by selecting films or film coatings for the cell-forming sheets forming the pouches, envelopes, pockets, and/or covering layer, that have the specifically desired permeability properties. Oxygen permeability can also be provided by perforating at least one of the films/film layer substrates with aeration holes before adding the compaction articles using, for example, at least one pin, preferably an array of from about 20 to about 60 pins, with, e.g., tapered points and diameters of from about 0.2 mm to about 1 mm, preferably from about 0.3 to about 0.6 mm. Alternatively, after the films/film layer substrates have been bonded together, enclosing the compaction articles in the pockets between them, one side of the heat cells may be perforated with aeration holes.

The required oxygen permeability of the films or film coatings for the present invention, regardless of the manner in which it is achieved, results in an oxygen diffusion into the heat cell during oxidation of the exothermic composition of from about 0.01 cc $O_2$/min./5 cm$^2$ to about 15 cc $O_2$/min./5 cm$^2$ (at 21° C., 1 ATM), preferably from about 0.9 cc $O_2$/min./5 cm$^2$ to about 2.0 cc $O_2$/min./5 cm$^2$ (at 21° C., 1 ATM). Although there is preferably provided aeration holes in the upper covering film/film layer, it is also possible to provide aeration holes in the lower covering film/film layer, and/or both.

The velocity, duration, and temperature of the thermogenic oxidation reaction of the heating element can be controlled as desired by changing the area of contact with air, more specifically, by changing the oxygen diffusion/permeability.

The heat cells of the present invention may optionally incorporate a component, such as a separate substrate layer or incorporated into at least one of the film layer substrates, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The heat cells may also comprise a separate substrate layer, or incorporated into at least one of the film layer substrates, a self-adhesive component and/or a sweat-absorbing component. A webbed or corrugated material, which will allow air to circulate between the skin and the heat cell to improve comfort to the wearer, may also be incorporated into at least one of the film layer substrates.

Secondary Packaging

These heat cells can be used alone, or can be incorporated into various wraps. Typically, these wraps have a means for retaining the wraps in place around various parts of the body, such as knee, neck, back, etc. and can comprise any number of styles and shapes.

The finished heat cell is packaged in a secondary air-impermeable package to prevent the oxidation reaction from occurring until desired as described in the aforementioned U.S. Pat. No. 4,649,895, already incorporated herein by reference. Alternatively, air impermeable removable adhesive strips can be placed over the aeration holes in the heat cells such that, when the strips are removed, air is allowed to enter the heat cell, thus activating the oxidation reaction of the iron powder.

EXAMPLES

The following examples further describe and demonstrate preferred embodiments within the scope of the present invention. The examples are given solely for the purpose of illustration, and are not to be construed as limitations of the present invention, as many variations thereof are possible without departing from its spirit and scope of the invention.

Example 1

A heat cell is prepared as follows. The following components are combined using conventional blending techniques to form a particulate composition.

| Ingredients | W/W % |
| --- | --- |
| Iron | 62.0 |
| Microcrystalline Cellulose | 15.0 |
| Activated Carbon | 9.0 |
| Maltitol Syrup | 6.0 |
| Sodium Chloride | 5.0 |
| Croscarmelose Sodium | 1.5 |
| Acrylic Acid-Starch Co-polymer | 1.5 |

Approximately 90 grams of carbon are mixed with approximately 50 grams of sodium chloride in a blender or mixer. Approximately 620 grams of iron and approximately 15 grams of croscarmellose sodium are added to the blender/mixer and mixed vigorously until the mixture is uniform. The mixture is then sprayed, while still being vigorously blended, with approximately 60 grams of maltitol syrup to form a dust-free agglomeration. Gentle blending is used to mix approximately 15 grams of acrylic acid-starch co-polymer into the agglomerated mixture. After the acrylic acid-starch co-polymer is uniformly dispersed, approximately 150 grams of microcrystalline cellulose is added. Gentle mixing is continued until all ingredients are uniformly distributed within the agglomerated mixture. The mixture is then transferred to a rotary tablet press and compressed, into disk-shaped tablets, having a hole passing perpendicular through the center of the top and bottom surfaces. The tablets have a density of greater than 2.0 g/cm$^3$, a thickness of approximately 0.35 cm, and a diameter of approximately 2 cm.

The tablet is added to the disk shaped, vacuum formed pocket in a sheet of LDPE film. A flat sheet of poly(ethylene-vinyl acetate), is then placed over the LDPE sheet having the pocket containing the tablet and the two sheets are heat bonded together, such that the tablet is enclosed within the pocket between the two sheets to form the heat cell. Water is injected by needle, through the polypropylene nonwoven/LDPE or/poly(ethylene-vinyl acetate) sheet, into the hole in the center of the tablet, until the total water content is approximately 20%, by weight of the tablet composition. The polypropylene nonwoven/LDPE sheet, is perforated to provide a diffusive $O_2$ permeability of about 1.7 cc/min./5 cm$^2$ (at 21° C., 1 ATM). The vacuum is released and the material around the heat cell is trimmed to provide a border of excess material around the perimeter of the cell. The cell begins to generate heat shortly after the perforation of the LDPE film. The resulting cell height is approximately 0.59 cm and the diameter is approximately 2.1 cm having a fill volume to cell volume ratio, after water is added, of approximately 0.89.

This cell can be incorporated into, for example, body wraps and/or packaged in air tight secondary packaging for future use.

Example 2

| Ingredients | W/W % |
| --- | --- |
| Iron | 68.5 |
| Microcrystalline Cellulose | 15.0 |
| Activated Carbon | 9.0 |
| Sodium Chloride | 5.0 |
| Corn Syrup | 2.5 |

Approximately 90 grams of carbon are mixed with approximately 50 grams of sodium chloride in a blender or mixer. Approximately 685 grams of iron and 30 grams of microcrystalline cellulose are added to the blender/mixer and blended vigorously until the mixture is uniform. The mixture is then sprayed, while still being blended vigorously, with approximately 25 grams of corn syrup to form a dust-free agglomeration. Approximately 120 grams of microcrystalline cellulose are added and gentle mixing is used until all the ingredients are uniformly distributed within the agglomerated mixture. The mixture is then transferred to a rotary tablet press and compressed, into disk-shaped tablets, having concaved top and bottom sides, i.e., double-whisper design. The tablets have a density of greater than 2.0 g/cm$^3$, a thickness of approximately 0.35 cm, and a diameter of approximately 2 cm. The tablet is added to the vacuum formed, disk shaped pocket and sealed between the top and bottom film sheets as described in Example 1. Water is injected by needle, through the LDPE sheet, into the concaved center of the tablet, until the total water content is approximately 22%, by weight of the tablet composition. The cell begins to generate heat shortly after the perforation of the LDPE film as described in Example 1. The cell height is approximately 0.59 cm and the diameter is approximately 2.2 cm. The resulting fill volume to cell volume ratio, after water is added, is approximately 0.89.

This cell can also be incorporated into, for example, body wraps and/or packaged in air tight secondary packaging for future use.

Example 3

A heat cell is prepared as follows.

| Ingredients | W/W % |
| --- | --- |
| Iron | 60.0 |
| Microcrystalline Cellulose | 19.0 |
| Activated Carbon | 9.0 |
| Maltitol Syrup | 6.0 |
| Sodium Chloride | 4.5 |
| Isobutylene Maleic Anhydride Co-polymer | 1.5 |

The above components are combined as described in Example 1, except isobutylene maleic anhydride co-polymer is used instead of acrylic acid-starch co-polymer as the water-holding material. The mixture is then transferred to a rotary tablet press and compressed, into disk-shaped tablets, having convexed top and bottom sides. The tablets have a density of greater than 2.0 g/cm$^3$, a thickness of approximately 0.4 cm, and a diameter of approximately 2 cm. Thirty pins of approximately 0.5 mm diameter are pressed simultaneously into the polypropylene nonwoven/LDPE or /poly(ethylene-vinyl acetate) sheet, which has been thermoformed to form a pocket for the heat cell, until they completely penetrate. This perforation process results in a diffusive $O_2$ permeability of about 1.7 cc/min./5 cm$^2$ (at 21° C., 1 ATM). The tablet is added to the disk shaped preformed pocket. Water is added dropwise to the tablet, until the total water content is approximately 20%, by weight of the tablet composition. A flat polypropylene nonwoven sheet coated with poly(ethylene-vinyl acetate), is then placed over the polypropylene nonwoven/LDPE sheet having the pocket containing the wetted tablet and heat bonded to the polypropylene nonwoven/poly(ethylene-vinyl acetate) sheet, such that the tablet is enclosed within the pocket between the two sheets to form the heat cell. Material around the heat cell is trimmed to provide a border of excess material around the perimeter of the cell. The cell height is approximately 0.62 cm and the diameter is approximately 2.1 cm. The resulting fill volume to cell volume ratio, after water is added, is approximately 0.95. The cell begins to generate heat shortly after adding the water.

This cell can also be incorporated into, for example, body wraps and/or packaged in air tight secondary packaging for future use.

Example 4

A heat cell is prepared as follows.

| Ingredients | W/W % |
| --- | --- |
| Iron | 64.0 |
| Microcrystalline Cellulose | 18.0 |
| Activated Carbon | 9.0 |
| Sodium Chloride | 5.0 |
| Corn Syrup | 2.5 |
| Acrylic Acid-Starch Co-polymer | 1.5 |

Approximately 90 grams of carbon are mixed with approximately 50 grams of sodium chloride in a blender or mixer. Approximately 15 grams of acrylic acid-starch co-polymer and approximately 18 grams of microcrystalline cellulose are blended into the mixture. Approximately 640 grams of iron are added to the blender/mixer and blended vigorously until the mixture is uniform. The mixture is then sprayed, while still being vigorously blended, with approximately 25 grams of corn syrup to form an agglomeration. Gentle mixing is used until all ingredients are uniformly distributed within the agglomerated mixture. The mixture is then transferred to a roller compactor and compressed into a ribbon having a density greater than 2.0 g/cm³. The ribbon is passed through an oscillating granulator set-up with a screen to collect granules of from about 180 microns to about 850 microns. The fines, which pass through the screen, as well as the granules larger than 850 microns, are recycled through the compactor. Approximately 2 grams of the granules are added to the disk shaped preformed pocket, which has been thermoformed to form the pocket, in a sheet of polypropylene nonwoven that has been coated with a film of LDPE. The cell height is 0.47 cm and the diameter is 2.5 cm. Water is added dropwise to the granules until the total water content is 22%, by weight of the granules. The resulting fill volume to cell volume ratio is approximately 0.99.

A flat polypropylene nonwoven/poly(ethylene-vinyl acetate) sheet is bonded to the bottom sheet, material around the heat cell is trimmed, and the heat cell perforated to allow a diffusive $O_2$ permeability of about 1 cc/min./5 cm² (at 21° C., 1 ATM), as described in Example 1. The cell begins to generate heat shortly after perforation.

This cell can also be incorporated into, for example, body wraps and/or packaged in air tight secondary packaging for future use.

Example 5

A heat cell is prepared as follows.

| Ingredients | W/W % |
|---|---|
| Iron | 77.0 |
| Microcrystalline Cellulose | 4.5 |
| Activated Carbon | 12.0 |
| Sodium Chloride | 4.0 |
| Corn Syrup | 2.5 |

Approximately 120 grams of carbon are mixed with approximately 40 grams of sodium chloride in a blender or mixer. Approximately 45 grams of microcrystalline cellulose are blended into the mixture. Approximately 770 grams of iron are added to the blender/mixer and blended vigorously until the mixture is uniform. The mixture is then sprayed, while still being vigorously blended, with approximately 25 grams of corn syrup to form an agglomeration. Gentle mixing is used until all ingredients are uniformly distributed within the agglomerated mixture and small granules are formed. Approximately 2.5 grams of the agglomerated granules are added to the disk shaped preformed pocket, which has been thermoformed to form the pocket, in a sheet of polypropylene nonwoven that has been coated with a film of LDPE. A flat polypropylene nonwoven/poly (ethylene-vinyl acetate) sheet is bonded to the bottom sheet, water is injected by needle to the granules until the total water content is 24%, by weight of the granules, material around the heat cell is trimmed, and the heat cell perforated to allow a diffusive $O_2$ permeability of about 1 cc/min./5 cm² (at 21° C., 1 ATM), as described in Example 3. The cell begins to generate heat shortly after perforation. The cell height is 0.47 cm and the diameter is 2.5 cm. The resulting fill volume to cell volume ratio is approximately 0.9.

Example 6

A heat cell is prepared as follows.

| Ingredients | W/W % |
|---|---|
| Iron | 75.0 |
| Microcrystalline Cellulose | 9.0 |
| Activated Carbon | 10.0 |
| Sodium Chloride | 3.0 |
| Corn Syrup | 3.0 |

Approximately 100 grams of carbon are mixed with approximately 30 grams of sodium chloride in a blender or mixer. Approximately 90 grams of microcrystalline cellulose are blended into the mixture. Approximately 750 grams of iron are added to the blender/mixer and blended vigorously until the mixture is uniform. The mixture is then sprayed, while still being vigorously blended, with approximately 30 grams of corn syrup to form an agglomeration. Gentle mixing is used until all ingredients are uniformly distributed within the agglomerated mixture and small granules are formed. Approximately 2.5 grams of the agglomerated granules are loosely compacted into a disk, then added to the disk shaped preformed pocket, which has been thermoformed to form the pocket, in a sheet of polypropylene nonwoven that has been coated with a film of LDPE. Water is added dropwise to the loose disk of granules until the total water content is 24%, by weight of the disk. A flat polypropylene nonwoven/poly(ethylene-vinyl acetate) sheet is bonded to the bottom sheet, material around the heat cell is trimmed, and the heat cell perforated to allow a diffusive $O_2$ permeability of about 1.7 cc/min./5 cm² (at 21° C., 1 ATM), as described in Example 3. The cell begins to generate heat shortly after perforation. The cell height is 0.47 cm and the diameter is 2.5 cm. The resulting fill volume to cell volume ratio is approximately 0.9.

This cell can also be incorporated into, for example, body wraps and/or packaged in air tight secondary packaging for future use.

Example 7

A heat cell is prepared as follows.

| Ingredients | W/W % |
|---|---|
| Iron | 70.0 |
| Microcrystalline Cellulose | 5.0 |
| Activated Carbon | 12.0 |
| Sodium Chloride | 4.0 |
| Maltitol Syrup | 7.0 |
| Acrylic Acid-Starch Co-polymer | 2.0 |

The above components are combined as described in Example 1. Gentle mixing is continued until all ingredients are uniformly distributed within the agglomerated mixture and granules are formed. The agglomerated granules are added to a rectangular shaped, vacuum formed pocket in a sheet of polypropylene nonwoven/LDPE film. A flat sheet of polypropylene nonwoven/poly(ethylene-vinyl acetate), perforated to provide a diffusive $O_2$ permeability of about 1.5 cc/min./5 cm² (at 21° C., 1 ATM), is then placed over the polypropylene nonwoven/LDPE sheet having the pocket containing the granules. The two sheets are heat bonded together, except for a small opening left unsealed in one end of the heat cell, such that the granules are enclosed within the pocket between the two sheets to form the heat cell.

Water is injected through the small opening, until the total water content is approximately 20%, by weight of the granular composition. The heat cell is flattened under a roller, from the sealed end to the open end, such that the air inside the heat cell is expelled through the small opening and perforated film. The small opening is then sealed by heat bonding. The vacuum is released and the material around the heat cell is trimmed to provide a border of excess material around the perimeter of the cell. The cell begins to generate heat shortly after the injection of the water. The resulting cell has a width of approximately 5 cm, a length of approximately 10 cm, a height of approximately 0.48 cm, and having a fill volume to cell volume ratio, after water is added, of approximately 1.0.

Due to the granule composition and flatting of the heat cell pocket, this cell will conform to the body surface and retain its shape/form even when vertical. This heat cell can be used as hand and/or foot warmers, or incorporated into body wraps, and/or packaged in air tight secondary packaging for future use.

Modifications of the above embodiments which are obvious to a person of ordinary skill in the art are intended to be within the scope of this invention.

What is claimed is:

1. An exothermic composition comprising:
   a.) from about 30% to about 80% by weight, of iron powder;
   b.) from about 3% to about 20% by weight, of carbonaceous material selected from the group consisting of activated carbon, non-activated carbon, and mixtures thereof;
   c.) from about 0% to about 9% by weight, of an agglomeration aid selected from the group consisting of gelatin, natural gums, cellulose derivatives, cellulose ether and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, maltitol syrup, and mixtures thereof; and
   d.) from about 4% to about 35% by weight of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;
   wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said composition comprises a physical form selected from the group consisting of dry agglomerated granules, direct compaction articles, and mixtures thereof.

2. An exothermic composition according to claim 1 wherein said dry binder comprises from about 7% to about 30% by weight, of microcrystalline cellulose.

3. An exothermic composition according to claim 1 further comprising from about 0.5% to about 10% by weight, of additional water-holding materials selected from the group consisting of acrylic acid salt starch co-polymer, isobutylene maleic anhydride co-polymer, vermiculite, carboxynethylcellulose, and mixtures thereof.

4. An exothermic composition according to claim 1 wherein said metal salt comprises sodium chloride.

5. An exothermic composition according to claim 1 wherein said compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid.

6. An exothermic composition according to claim 5 wherein said tablets and slugs comprise a disk shaped geometry having a diameter of from about 0.2 cm to about 10 cm and a height of from about 0.08 cm to about 0.7 cm.

7. An exothermic composition according to claim 6 wherein said direct compaction articles comprise a density of greater than about 1 $g/cm^3$.

8. An exothermic composition according to claim 7 wherein said tablets comprise a geometric shape selected from the group consisting of a disk shape wherein a hole passes perpendicular to and through the middle of the top and bottom surfaces and a disk shape wherein the top and bottom surfaces are concaved forming a reservoir conducive to holding a liquid.

9. An exothermic composition according to claim 8 wherein said tablets comprise a disk shape wherein a hole passes perpendicular to and through the middle of the top and bottom surfaces.

10. An exothermic composition according to claim 9 wherein said compaction articles comprise a density of from about 1.5 $g/cm^3$ to about 3.0 $g/cm^3$.

11. An exothermic composition according to claim 1 further comprising:
    a.) a unified structure comprising at least two opposed surfaces of cell-forming materials capable of forming a pocket using mechanical means, heat, vacuum, and mixtures thereof; and
    b.) a shape selected from the group consisting of a disk, triangle, pyramid, cone, sphere, square, cube, rectangle, rectangular parallelepiped, cylinder, and ellipsoid.

12. An exothermic composition according to claim 11 wherein said composition is sealed in said pocket between said opposed surfaces and wherein at least one of said opposed surfaces is air permeable and further wherein said composition is activated by the addition of an aqueous solution.

13. An exothermic composition according to claim 12 wherein said cell-forming materials are selected from the group consisting of films, nonwoven fabric laminated with a film layer substrate, web material comprising continuous filaments of thermoplastic resin laminated with a thermoplastic resin film, and mixtures thereof.

14. An exothermic composition according to claim 13 wherein said cell-forming materials are films selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

15. An exothermic composition according to claim 14 wherein at least one of said cell-forming materials are made air-permeable by perforating said cell-forming materials with at least one aeration hole having a diameter of from about 0.2 mm to about 1 mm.

16. An exothermic composition according to claim 15 comprising the shape of a disk having a diameter of from about 0.2 cm to about 10 cm and a height of from about 0.15 cm to about 1 cm and a cell volume of from about 0.0047 $cm^3$ to about 79 $cm^3$.

17. An exothermic composition according to claim 1 wherein said agglomeration aid comprises from about 0.5% to about 8% by weight, of an agglomeration aid selected from the group consisting of corn syrup, maltitol syrup, crystallizing sorbitol syrup, amorphous sorbitol syrup, and mixtures thereof.

18. An exothermic composition according to claim 12 made in the form of heat cells comprising the steps of:
   a.) mixing a particulate exothermic composition comprising powdered iron, dry powdered carbonaceous material, and an agglomeration aid to form an agglomeration;
   b.) mixing a dry binder to said agglomeration to form an agglomerated pre-compaction composition;
   c.) compacting and forming said pre-compaction composition into direct compaction articles selected from the group consisting of granules, pellets, tablets, slugs, and mixtures thereof;
   d.) packing said compaction articles into a pocket formed between a bottom cell-forming surface and a top cell-forming surface wherein at least one surface is oxygen permeable; and
   e.) sealing said pocket wherein said compaction articles are sealed between the two surfaces forming a unified structure comprising at least two opposed surfaces;
   wherein said compaction articles are activated by the addition of an aqueous solution and wherein said exothermic composition additionally comprises a metal salt added to said agglomeration or added subsequently as said aqueous solution.

19. An exothermic composition according to claim 18 wherein from about 10% to about 50% by weight of said compaction articles, of said aqueous solution is added to said heat cells.

20. An exothermic composition according to claim 12 made in the form of heat cells comprising the steps of:
   a.) mixing a particulate exothermic composition comprising powdered iron, dry powdered carbonaceous material, and an agglomeration aid to form an agglomeration;
   b.) packing said agglomeration into a pocket formed between a bottom cell-forming surface and a top cell-forming surface wherein at least one surface is oxygen permeable; and
   c.) sealing said pocket forming a unified structure comprising at least two opposed surfaces wherein said agglomeration is sealed between the two surfaces;
   wherein said agglomeration is activated by the addition of an aqueous solution and wherein said exothermic composition additionally comprises a metal salt added to said agglomeration or added subsequently as said aqueous solution.

21. An exothermic composition according to claim 20 wherein from about 10% to about 50% by weight of said agglomeration, of said aqueous solution is added to said heat cells.

* * * * *